(12) United States Patent
Figley

(10) Patent No.: US 6,602,213 B1
(45) Date of Patent: Aug. 5, 2003

(54) DISPOSABLE SPLINT WITH INSTANT COLD PACK

(76) Inventor: Sara N. Figley, 322 Rolling Hills La., San Marcos, CA (US) 92069

( * ) Notice: Subject to any disclaimer, the term of this patent is extended or adjusted under 35 U.S.C. 154(b) by 0 days.

(21) Appl. No.: 09/588,092

(22) Filed: May 25, 2000

(51) Int. Cl.$^7$ .................................................. A61F 5/00
(52) U.S. Cl. ........................... 602/5; 607/96; 607/108; 607/114; 602/14
(58) Field of Search ................................. 128/846, 869, 128/878, 879, 882; 602/5, 14; 607/108, 111, 112, 114

(56) References Cited

U.S. PATENT DOCUMENTS

| | | | |
|---|---|---|---|
| 2,773,531 A | * 12/1956 | Johnson | 607/112 |
| 2,907,173 A | 10/1959 | Robbins | 62/4 |
| 3,561,435 A | 2/1971 | Nicholson | 128/82.1 |
| 3,624,745 A | 11/1971 | Bowers | 128/93 |
| 3,901,225 A | 8/1975 | Sconce | 128/89 |
| 3,977,202 A | 8/1976 | Forusz | 62/4 |
| 4,834,802 A | * 5/1989 | Prier | 604/291 |
| 4,886,063 A | * 12/1989 | Crews | 607/112 |
| 4,971,041 A | 11/1990 | Millikan et al. | 128/87 |
| 5,065,758 A | 11/1991 | Whitehead | 128/402 |
| 5,395,399 A | * 3/1995 | Rosewald | 607/112 |
| 5,887,437 A | * 3/1999 | Maxim | 607/112 |
| 6,099,555 A | * 8/2000 | Sabin | 607/96 |

* cited by examiner

Primary Examiner—Michael A. Brown
(74) Attorney, Agent, or Firm—John R. Ross; John R. Ross, III

(57) ABSTRACT

A disposable splint that has a brace, at least one instant cold pack, and an attachment means for attaching the brace and the at least one instant cold pack to a wearer's limb. In a preferred embodiment, the disposable splint is secured to the wearer's limb via an elastic wrap. Also in a preferred embodiment the brace portion is foldable and comprises a bottom brace portion and two side brace portions. Also in a preferred embodiment, the instant cold pack is fixedly attached to the brace portion via a hook and loop connection.

27 Claims, 3 Drawing Sheets

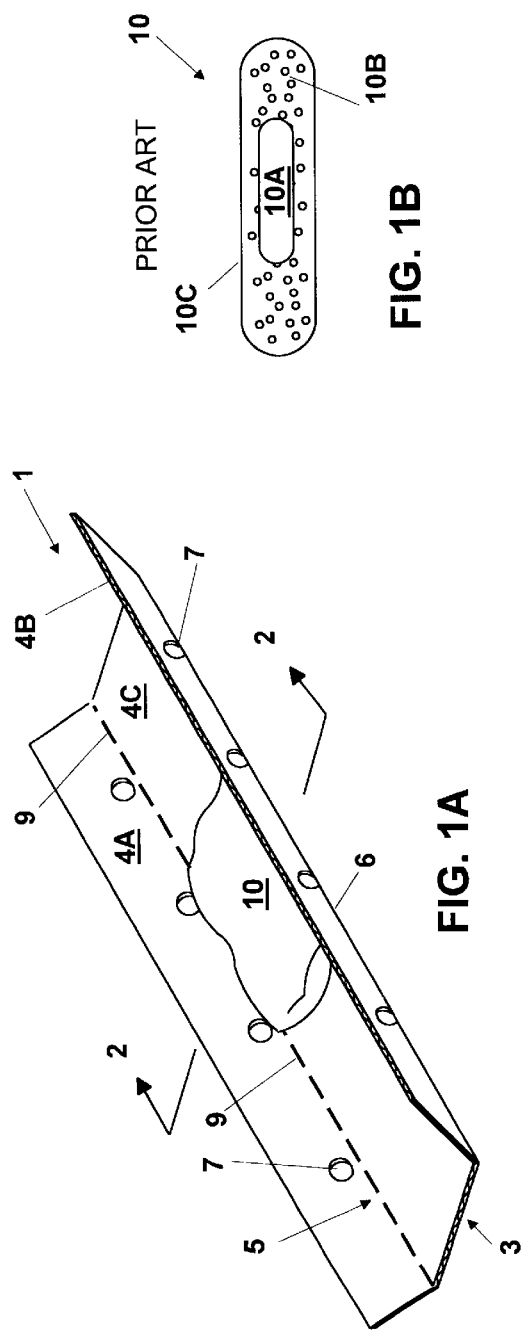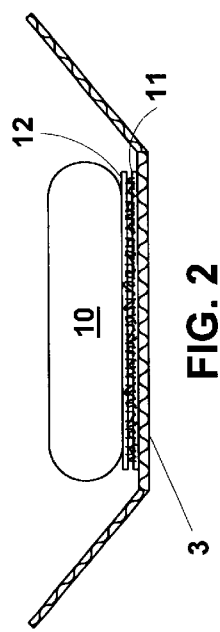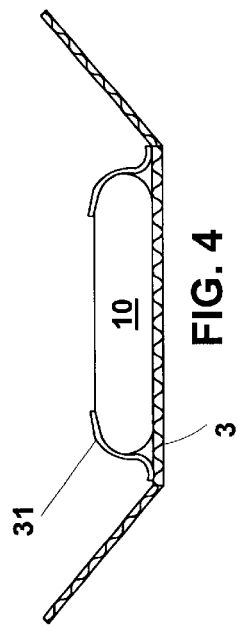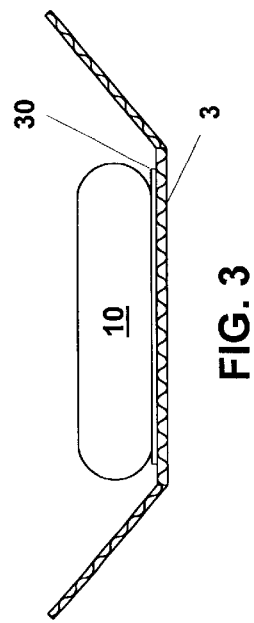

DISPOSABLE SPLINT WITH INSTANT COLD PACK

BACKGROUND OF THE INVENTION

Prior Art Treatment for Injured Arms and Legs

Injuries to the body, such as a broken arm, a broken leg or an ankle strain, are common to people all over the world. It is well known that to adequately treat such an injury, the injured part of the body should be elevated, immobilized and cooled with a cooling device. Normally, the method of treating the injury involves splinting the injured area to prevent movement, applying ice to the injured area and raising the injured area to minimize swelling.

Currently, there are a number of devices available that combine a splint with an ice bag to provide a single device that encompasses both features. U.S Pat. No. 3,561,435 discloses an inflatable splint with a container for the holding of ice. U.S. Pat. No. 3,901,225 discloses an inflatable splint with a plurality of spaced apart pockets for containing hot or cold therapeutic substances. U.S. Pat. No. 4,971,041 discloses an apparatus for supporting and protecting the limb of a patient wherein provisions may be made for heat/ice packs by providing pockets on the inside of the wrap. U.S. Pat. No. 5,065,758 discloses a cold pack for treating an injury wherein BLUE ICE is encased in elongated plastic closed end cylinders and the cylinders are inserted in parallel pockets formed in a wrapper.

Disposable Splints

Disposable Splints are also known. A disposable splint is relatively inexpensive to make and can be thrown away after a minimal number of uses (for usually one use). U.S. Pat. No. 3,624,745 discloses a disposable splint formed from a heavy, bendable sheet material such as cardboard, or the like, that may be carried in a flattened condition to the scene of the accident. Also, DynaMed Co. with offices in Carlsbad, Calif. makes a similar disposable cardboard splint. Cardboard is an ideal material for disposable splints because it is relatively inexpensive, sturdy, and lightweight and readily available from a variety of sources.

Disposable splints tend to be simpler in design than reusable splints and therefore usually are less expensive. Hence, after a disposable splint is used, rather than worrying about cleaning the splint, it can be thrown away. Unfortunately, however, current disposable splints have no provisions for accommodating ice bags or other cooling devices. Instead, typically, the injury is first splinted using the prior art disposable splint, and then ice is either held next to the injured area or ice is wrapped around the injury with a separate wrapping device.

Instant Cold Packs

Ice bags are well known. They are bags that are filled with normal ice (frozen water) and require refrigeration before they become cold. Cold packs are also well known. A cold pack is usually filled with chemicals other than water to lengthen the amount of time that the cold pack stays cold after refrigeration. However, they still require refrigeration to become cold.

Instant cold packs (also known as "instant ice packs") are known in the prior art. They are easily distinguished from ice bags or cold packs in that the instant cold pack requires no refrigeration. Instead, the instant cold pack consists of chemicals in a bag containing two or more compartments that function to keep the chemicals separated until activation is desired. Activation is achieved by rupturing or removing the separating means to produce an endothermic reaction, that is, as a result of the chemical reaction, cold is produced by the absorption of heat from the surroundings.

There are several instant cold packs disclosed in the prior art. U.S. Pat. No. 2,907,173 discloses a refrigeration package comprising an outer sealed envelope coated with metallic foil and containing a dry freezing chemical mixture, and another sealed envelope within the outer sealed envelope, wherein the other sealed envelope contains a hydrous substance and is rupturable without breaking the outer envelope. U.S. Pat. No. 3,977,202 discloses a similar instant cold pack comprising ammonium nitrate, sodium acetate trihydrate and an aqueous solution of ethylene glycol wherein the components are separated until activation is desired, but when activated by admixing, an endothermic reaction occurs resulting in a lowering of the temperature of the device. Also, Allegiance Healthcare Corp, with offices in McGraw Park, Ill. currently offers an instant cold pack that relies on the interaction of water and ammonium nitrate to provide cold. Thera-Med, Inc., with offices in Waco, Tex. offers an instant cold pack that also relies on the interaction of water and anmuonium nitrate to provide cold.

FIG. 1B shows a cross section view of prior art instant cold pack 10. Water-filled thin plastic bag 10A fits inside sturdy plastic bag 10C. Ammonium nitrate 10B surrounds plastic bag 10A. The user activates instant cold pack 10 by squeezing it. This causes water-filled thin plastic bag 10A to rupture. The water and ammonium nitrate 10B interact chemically and cold is produced.

Because instant cold packs become "cold" due to a chemical reaction, they are only cold for a short amount of time. For example, the Allegiance instant cold pack referred to above provides a temperature of 33 degrees F for 30 minutes. Therefore, after an instant cold pack has been used (i.e., the chemical reaction has occurred), it is usually disposed of.

What is needed is a better disposable splint.

SUMMARY OF THE INVENTION

The present invention provides a disposable splint that has a brace, at least one instant cold pack, and an attachment means for attaching the brace and the at least one instant cold pack to a wearer's limb. In a preferred embodiment, the disposable splint is secured to the wearer's limb via an elastic wrap. Also in a preferred embodiment the brace portion is foldable and comprises a bottom brace portion and two side brace portions. Also in a preferred embodiment, the instant cold pack is fixedly attached to the brace portion via a hook and loop connection.

BRIEF DESCRIPTION OF THE DRAWINGS

FIG. 1A shows a preferred embodiment of the present invention.

FIG. 1B shows a prior art instant cold pack

FIG. 2 shows a cross section view of the preferred embodiment shown in FIG. 1A.

FIG. 3 shows a cross section view of another preferred embodiment.

FIG. 4 shows a cross section view of another preferred embodiment.

DETAILED DESCRIPTION OF THE PREFERRED EMBODIMENT

A detailed description of a preferred embodiment of the present invention can be seen by reference to FIGS. 1A–12.

FIG. 1A shows a first preferred embodiment of the present invention. Splint 1, as shown in FIG. 1A, is a leg splint and is preferably approximately 24 inches in length. Brace 3 is bent along folds 5 and 6 to form bottom brace portion 4C and two side brace portions 4A and 4B, respectively. Preferably, brace 3 is made out of corrugated cardboard. Also, preferably, alternating cuts 9 are cut into brace 3 to make it easier to fold brace 3 at folds 5 and 6.

Figure 8:
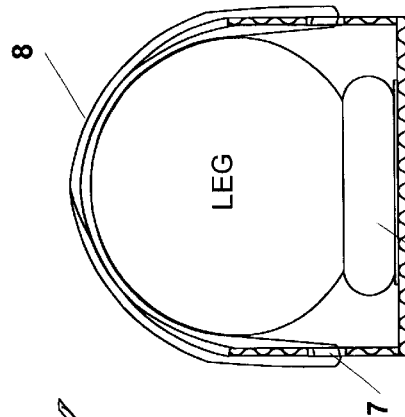
FIG. 8 shows a preferred embodiment of the present invention attached to a leg.

Holes 7 are cut into brace portions 4A and 4B so that elastic bandage 8 can be threaded through splint 1 when splint 1 is applied to a victim, as shown in FIG. 8.

Instant cold pack 10 is fixedly attached to brace 3. FIG. 2 shows a preferred method of fixedly attaching instant cold pack 10 to brace 3. Instant cold pack 10 is attached to brace 3 through a Velcro® connection. Velcro® refers generally to the hook and loop structure that when pressed together provides that two parts carrying the Velcro® are releasably joined. Velcro® loop section 11 is adhered to brace 3. Velcro® hook section 12 is adhered to instant cold pack 10. By pressing together loop section 11 and hook section 12, instant cold pack 10 becomes fixedly attached to brace 3.

Use of the Present Invention

Figure 10:
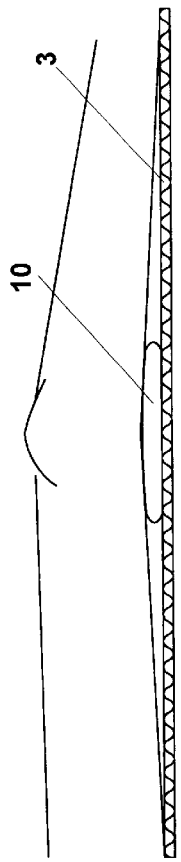
FIG. 10 shows a side view of a preferred embodiment of the present invention.

After an injury occurs and before applying disposable splint 1, instant cold pack 10 first needs to be activated. As explained in the background section, squeezing activates instant cold pack 10. After instant cold pack 10 has been activated, the injured limb is splinted. FIG. 10 shows a side view of a leg splinted by brace 3. Instant cold pack 10 is underneath the knee and on top of brace 3. FIG. 8 shows a cross section view of the leg supported by brace 3. Instant cold pack 10 is underneath the knee and elastic bandage 8 is threaded through holes 7 so that disposable splint 7 is firmly attached to the leg.

Figure 5:
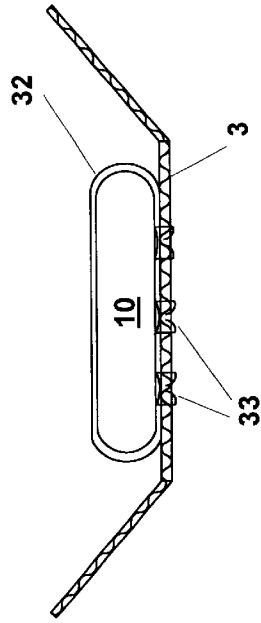
FIG. 5 shows a cross section view of another preferred embodiment.

Alternate Embodiments of the Present Invention
Other Methods of Attaching the Instant Cold Pack Although the preferred embodiment shown in FIG. 2 shows Velcro® attaching instant cold pack 10 to brace 3, there are many other ways in which instant cold pack 10 could be attached. For example, FIG. 3 shows instant cold pack 10 attached to brace 3 with double-sided tape 30. FIG. 4 shows instant cold pack 10 attached to brace 3 with single-sided tape 31. FIG. 5 shows cloth pocket 32 stapled to brace 3 via staples 33. Instant cold pack 10 is then slid inside cloth pocket 32.

Covering the Top of the Instant Cold Pack

Figure 6:
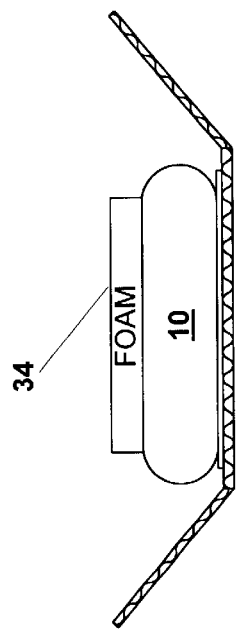
FIG. 6 shows a cross section view of another preferred embodiment with foam attached to the top of the instant cold pack.

FIG. 6 shows another preferred embodiment in which the top of instant cold pack 10 is covered by foam 34. The covering of instant cold pack 10 with foam lessens the amount of cold transferred to the injury and provides greater comfort to the wearer of the disposable splint.

Multiple Instant Cold Packs

Figure 7:
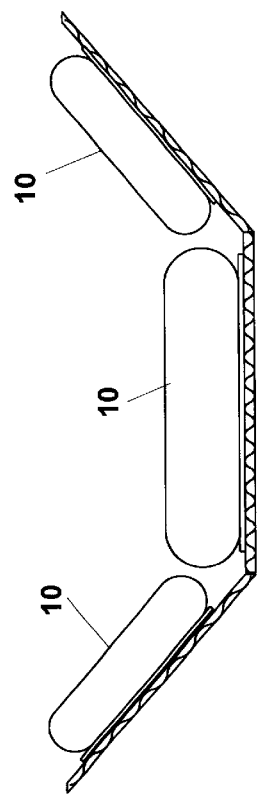
FIG. 7 shows a cross section view of another preferred embodiment with multiple instant cold packs.

FIG. 7 shows multiple instant cold packs 10 attached to brace 3. This allows for greater coverage of cold to the injured limb.

Holeless Brace Portion

Figure 9:
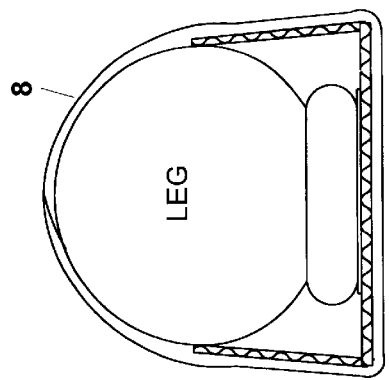
FIG. 9 shows another preferred embodiment of the present invention attached to a leg.

Although FIGS. 1 and 8 show holes 7 in brace 3, it is also possible to make a disposable splint 1 without holes 7. FIG. 9 shows elastic wrap 9 wrapped completely around brace 3 and the leg of the splint wearer.

Brace Portion with Multiple Folds

Figure 12:
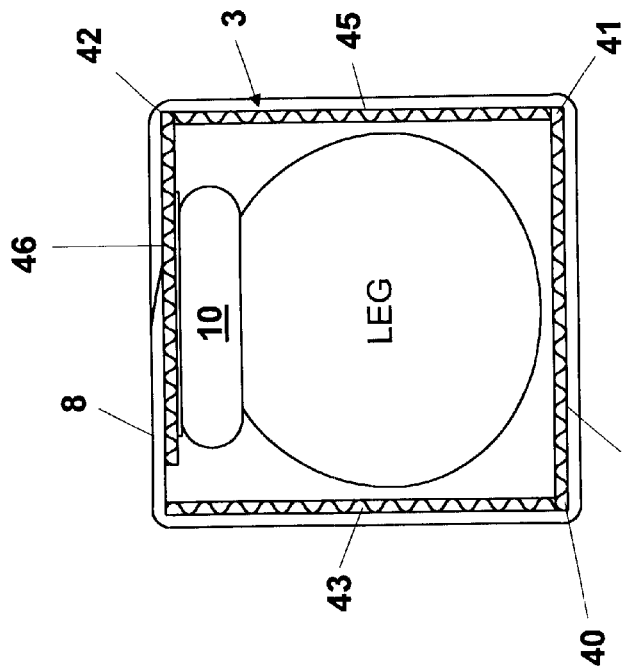
FIG. 12 shows a cross section view of the embodiment shown in FIG. 11.

Although FIG. 1A shows folds 5 and 6 in brace 3 to form side brace portions 4A and 4B and bottom brace portion 4C, it is also possible to increase the number of folds, thereby increasing the number of brace portions. For example, FIG. 12 shows brace 3 folded at folds 40, 41 and 42. These folds form bottom brace portion 44, top brace portion 46 and two side brace portions 43 and 45. Elastic wrap 8 is completely wrapped around brace 3 to secure the disposable splint to the wearer's leg.

Figure 11:
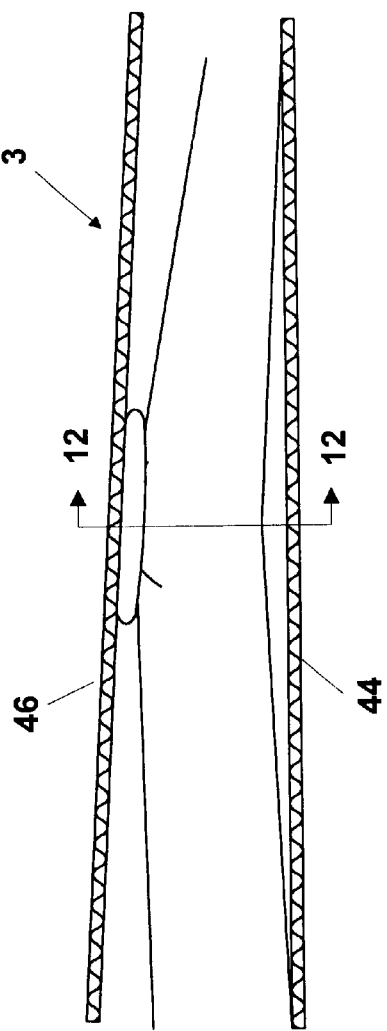
FIG. 11 shows a side view of another preferred embodiment of the present invention.

This embodiment is advantageous if the ice needs to be applied to the top of the knee as shown in FIGS. 11 and 12, rather than underneath the knee as shown in FIGS. 10 and 8. FIG. 11 shows a side view of the embodiment shown in FIG. 12. Instant cold pack 10 is attached to top brace portion 46 and is in contact with the top of the wearer's knee.

While the above description contains many specifications, the reader should not construe these as limitations on the scope of the invention, but merely as exemplifications of preferred embodiments thereof. Those skilled in the art will envision many other possible variations are within its scope. For example, although the present invention is can be disposed of after its first use, those of ordinary skill in the art will recognize that under certain situations it may be desirable to save the brace portion if it has not been too extensively damaged. For example, after using the embodiment shown in FIG. 2, it would be easy to substitute an unused instant cold pack 10 after the first instant cold pack 10 had been activated and was no longer capable of providing cold. The unused instant cold pack 10 could be attached via the Velcro® connection shown in FIG. 2. Also, although the previous embodiments disclosed using the present invention for a knee injury, those of ordinary skill in the art will recognize that the present invention could be utilized in conjunction with other parts of the wearer's body (for example, the arm, the ankle, or the wrist). The size of the present invention would be modified so that it appropriately supports the injured part of the body. Accordingly the reader is requested to determine the scope of the invention by the appended claims and their legal equivalents, and not by the examples which have been given.

I claim:

1. A disposable splint, comprising:

A) a rigid brace for immobilizing a wearer's limb,

B) at least one instant cold pack, said instant cold pack comprising at least two substances in separate compartments and separated by a breakable barrier, wherein cold is produced by an endothermic reaction caused by the breaking of said breakable barrier and the mixing of said at least two substances, and C) an attaching means for attaching said brace and said at least one instant cold pack to said wearer's limb.

2. The disposable splint as in claim 1, wherein said at least two substances are ammonium nitrate and water.

3. The disposable splint as in claim 1, wherein said at least two substances are three substances, wherein said three substances are ammonium nitrate, sodium acetate trihydrate and an aqueouys solution of ethylene glycol.

4. The disposable splint as in claim 1, wherein said attaching means is a wrapping device for securing the disposable splint to the wearer's limb.

5. The disposable splint as in claim 4, wherein the wrapping device is an elastic wrap.

6. The disposable splint as in claim 1, wherein said brace is made of corrugated cardboard.

7. The disposable splint as in claim 1, wherein said brace is foldable at at least one fold.

8. The disposable splint as in claim 7, wherein said at least one fold is two folds and said brace comprises:

A) a bottom brace portion, and

B) two side brace portions.

9. The disposable splint as in claim 7, wherein said at least one fold is three folds and said brace comprises:

A) a bottom brace portion,

B) a top brace portion, and

C) two side brace portions.

10. The disposable splint as in claim 1, wherein said instant cold pack is fixedly attached to said brace.

11. The disposable splint as in claim 10, wherein said instant cold pack is fixedly attached to said brace via a hook and loop connection.

12. The disposable splint as in claim 10, wherein said instant cold pack is fixedly attached to said brace via double-sided tape.

13. The disposable splint as in claim 1, wherein said instant cold pack is fixedly attached to said brace via single-sided tape.

14. The disposable splint as in claim 1, wherein said instant cold pack is fixedly attached to said brace via a cloth pocket stapled to said brace.

15. A method for splinting a limb injury of a wearer, comprising the steps of:

A) obtaining a disposable splint, comprising:

1. a rigid brace for immobilizing a wearer's limb, and 2. at least one instant cold pack attached to said brace, said instant cold pack comprising at least two substances in separate compartments and separated by a breakable barrier, wherein cold is produced by an endothermic reaction caused by the breaking of said breakable barrier and the mixing of said at least two substances, wherein said disposable splint is capable of being secured to said wearer's limb, B) activating said instant cold pack, and C) securing said disposable splint to the injury on wearer's limb.

16. The method as in claim 15, wherein said disposable splint is secured to the wearer's limb via a wrapping device.

17. The method as in claim 16, wherein said wrapping device is an elastic wrap.

18. The method as in claim 15, wherein said brace is made of corrugated cardboard.

19. The method as in claim 15, wherein said brace is foldable at at least one fold.

20. The method as in claim 19, wherein said at least one fold is two folds and said brace comprises:

A) a bottom brace portion, and

B) two side brace portions.

21. The method as in claim 19, wherein said at least one fold is three folds and said brace comprises:

A) a bottom brace portion,

B) a top brace portion, and

C) two side brace portions.

22. The method as in claim 15, wherein said instant cold pack is fixedly attached to said brace.

23. The method as in claim 22, wherein said instant cold pack is fixedly attached to said brace via a hook and loop connection.

24. The method as in claim 22, wherein said instant cold pack is fixedly attached to said brace via double-sided tape.

25. The method as in claim 22, wherein said instant cold pack is fixedly attached to said brace via single-sided tape.

26. The method as in claim 22, wherein said instant cold pack is fixedly attached to said brace via a cloth pocket stapled to said brace.

27. A disposable splint, comprising:

A) a rigid means for immobilizing a wearer's limb,

B) at least one instant cold pack means, said instant cold pack means comprising at least two substances in separate compartments and separated by a breakable barrier, wherein cold is produced by an endothermic reaction caused by the breaking of said breakable barrier and the mixing of said at least two substances, and C) an attaching means for attaching said means for immobilizing a wearer's limb and said at least one instant cold pack means to said wearer's limb.

* * * * *